United States Patent [19]

Page et al.

[11] Patent Number: 4,655,971
[45] Date of Patent: Apr. 7, 1987

[54] NOVEL PROCESS FOR THE PREPARATION OF STEROIDAL ESTERS

[75] Inventors: Philip R. Page, Parede; William Heggie, Barreiro, both of Portugal

[73] Assignee: Plurichemie Anstalt, Liechtenstein

[21] Appl. No.: 641,267

[22] Filed: Aug. 16, 1984

Related U.S. Application Data

[63] Continuation-in-part of Ser. No. 402,548, Jul. 28, 1982, abandoned.

[30] Foreign Application Priority Data

Aug. 4, 1981 [PT] Portugal .................................. 73479
Oct. 22, 1981 [PT] Portugal .................................. 73864

[51] Int. Cl.$^4$ .................................................. C07J 17/00
[52] U.S. Cl. .................................................. 260/397.45
[58] Field of Search .................................. 260/397.45

[56] References Cited

U.S. PATENT DOCUMENTS

| | | | |
|---|---|---|---|
| 3,312,590 | 4/1967 | Elks et al. | 260/397.45 |
| 4,024,131 | 5/1977 | Villax | 260/397.46 |
| 4,176,126 | 11/1979 | Annen et al. | 260/397.45 |

FOREIGN PATENT DOCUMENTS 1443957  1/1970  Fed. Rep. of Germany .................. 260/397.45

Primary Examiner—Elbert L. Roberts
Attorney, Agent, or Firm—Ostrolenk, Faber, Gerb & Soffen

[57] ABSTRACT

A process for the preparation of corticosteriod esters of the formula

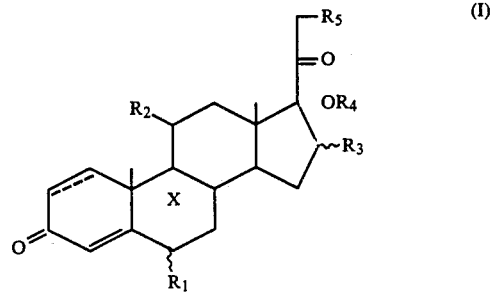

in which
---- signifies that a double bond can be present;
X is hydrogen, chlorine or fluorine;
$R_1$ is hydrogen, fluorine, chlorine or methyl, which may be either $\alpha$ or $\beta$;
$R_2$ is halogen, oxo or hydroxyl;
or $R_3$ is hydrogen, $\alpha$-methyl or $\beta$-methyl;
or $R_2$ and X jointly form an epoxide group;
$R_4$ is an acyl group of the formula RCO, in which R is one of the following
  (i) an alkyl group containing 1 to 16 carbon atoms, whether straight-chained, branched or cyclic;
  (ii) an aralkyl group of 7 to 8 carbon atoms;
  (iii) a phenyl group;
$R_5$ is hydroxyl or $R_6$; where
$R_6$ is hydrogen, one or two halogen atom substituents or $OR_7$, where $R_7$ is an acyl group of the formula R'CO in which R', which can be identical or different to R in the same molecule, is one of the following:
  (i) an alkyl group of 1 to 16 carbon atoms, whether straight-chained, branched or cyclic;
  (ii) an aralkyl group of 7 to 8 carbon atoms; or
  (iii) a phenyl group.
which comprises esterifying a compound of the formula

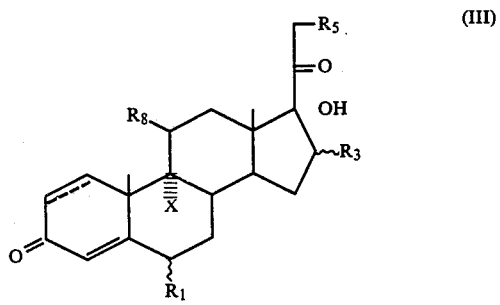

wherein X, $R_1$, $R_3$ and $R_5$ are as defined above, and $R_8$ is trihaloacetate, halogen or oxo, or jointly forms an epoxide group with X;
at the 17-position only, or at the 17- and 21-positions when $R_5$ in formula III is hydroxyl, the said esterification being carried out with the anhydride of the acid containing the group desired.

25 Claims, No Drawings

NOVEL PROCESS FOR THE PREPARATION OF STEROIDAL ESTERS

This is a continuation-in-part of application Ser. No. 402,548, filed July 28, 1982, now abandoned.

This invention relates to a process for the preparation of steroidal esters, and to certain of such steroidal esters, which are novel per se.

Corticosteroids have long been known for their anti-inflammatory activity. It has been similarly known that the topical activity can be considerably enhanced by the introduction of ester functions, especially at the 17-position only and at the 17- and 21-positions. These esterified corticosteroids also offer the advantage of minimal systemic activity.

The present invention provides a new and efficient route to compounds of the following formula:

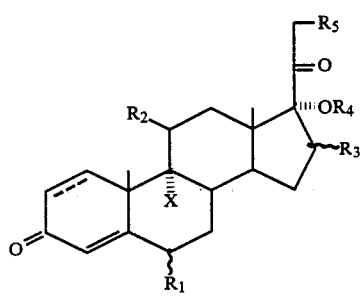

(I)

in which
- - - - signifies that a double bond can be present;
X is hydrogen, chlorine or fluorine;
$R_1$ is hydrogen, fluorine, chlorine or methyl, which may be either $\alpha$ or $\beta$;
$R_2$ is halogen, oxo or hydroxyl;
$R_3$ is hydrogen, $\alpha$-methyl or $\beta$-methyl;
$R_2$ and X jointly form an epoxide group;
$R_4$ is an acyl group of the formula RCO, in which R is one of the following:
  (i) an alkyl group containing 1 to 16 carbon atoms, whether straight-chained, branched or cyclic;
  (ii) an aralkyl group of 7 to 8 carbon atoms; or
  (iii) a phenyl group;
$R_5$ is hydroxyl or $R_6$; where
$R_6$ is hydrogen, one or two halogen atom substituents or $OR_7$, where $R_7$ is an acyl group of the formula R'CO in which R', which can be identical or different to R in the same molecule, is one of the following:
  (i) an alkyl group of 1 to 16 carbon atoms, whether straight-chained, branched or cyclic;
  (ii) an aralkyl group of 7 to 8 carbon atoms; or
  (iii) a phenyl group.

Thus, the present invention covers the preparation of betamethasone, dexamethasone, beclomethasone, clobetasol, prednisolone, hydrocortisone esters by one general process.

The known prior art processes available for the preparation of such compounds can be split into three groups.

The first is the direct introduction of 17-ester function, without any protection at, for instance, the 11-position. This was exemplified by Huang-Minlon et al. in J. Amer. Chem. Soc. 74, 5394–96 (1952) and in British Pat. Nos. 737,291 (priority 1952) and 1,070,751 (priority 1964), and U.S. Pat. No. 3,721,687 (priority 1970). The acylation was carried out with the anhydride of a lower aliphatic carboxylic acid, in the presence of a strong acid catalyst, such as p-toluenesulphonic acid.

It is well known that the order of esterification of hydroxyl functions is primary hydroxyls, then secondary and finally tertiary. Thus, in the case of an 11,17,21-trihydroxy steroid, direct esterification will give a mixture made up of some varying percentages of the 21-monoester, 11,21-diester and 11,17,21-triester. The separation of the required product is normally not economically feasible, even if a suitable process can be found. Additionally, no method for the selective removal of an unactivated 11-ester in an 11,17,21-triester is at present known.

The second methodology covers the use of functional group protection prior to the introduction of the ester function(s). The usual protecting groups for the 11-hydroxyl function were the trihaloacetate, the trimethylsilyl ether, the tetrahydropyran-(2'-yl) ether, and the nitrate ester. The first of these was initially described by Reichstein in U.S. Pat. No. 2,800,489 (priority 1953), and has been used in British Pat. No. 1,097,165 (priority 1965) and U.S. Pat. No. 4,024,131 (priorities 1974 and 1975). The trimethylsilyl ether was used in British Pat. No. 1,227,992 (priority 1968), wherein the preparative method involved extraction techniques, which are in preference to be avoided, whilst the yields given are not particularly good. The tetrahydrofuran-(2'-yl) ether group was described in U.S. Pat. No. 4,024,131 and similarly the preparative method involved extraction techniques. Nitrate ester protection was first described in British Pat. No. 1,082,573 (priority 1965) and then again in British Pat. No. 1,158,492 (priority 1966). In the latter disclosure it was stated that the technique was not universally applicable, especially for 21-desoxy steroids, due to the formation of the 17-nitrate ester.

Once the 11-hydroxyl group and any other sensitive groups have been protected, the 17-acylation is carried out. The first process to be used was that given in British Pat. No. 737,291, using the anhydride of a lower carboxylic acid in the presence of a strong acid catalyst, such as p-toluenesulphonic acid. This process was further used in British Pat. Nos. 1,158,492 and 1,227,992, amongst others. Unfortunately, the process suffers from the disadvantage that it is necessary "to carry out the acylation by heating the 17α-hydroxy-20-keto steroid with the anhydride at temperatures in excess of 100° C. for extended periods of time". This causes extensive degradation, especially in steroids containing many sensitive functional groups.

Hence, this process was superseded by the use of an aliphatic or cycloaliphatic carboxylic acid together with trifluoroacetic anhydride, as described in German Pat. No. 1,013,284 (priority 1956), and used in British Pat. Nos. 1,391,712 (priority 1971) and 1,158,492 and 1,227,992 amongst others. However, this method was only a slight improvement over the then prior art, since it was still necessary to heat the reaction mixture, this time to between 80° C. and 90° C.

British Pat. No. 1,097,165 (priority 1965) then described a process which is basically a combination of the two given above in that an aliphatic or cycloaliphatic carboxylic acid containing from one to nine carbon atoms, plus trifluoroacetic anhydride and a strong acid catalyst, such as p-toluenesulphonic acid, are used to effect the desired acylation. It was claimed that this mixture worked at room temperature, making it more applicable than the then prior art. Unfortunately, the quantity of reagents necessary was extremely high, typically ten milliliters of the acid and four milliliters of trifluoroacetic anhydride per gram of the starting steroid. This not only made the process expensive, but it then became difficult to isolate the desired product in a pure state. Hence, the mixtures had to be steam-distilled to remove the vast excess of the acids and then column chromatography was normally used to isolate the products.

After the 17-acylation step it is then necessary to selectively remove the 11-protecting group. A trifluoroacetate group can be removed by solvolysis with silica, as described in British Pat. No. 1,391,712 and in U.S. Pat. No. 4,024,131; by sodium bicarbonate hydrolysis, as described in U.S. Pat. No. 4,024,131; by solvolysis with an alkali or alkaline earth metal salt of an acid with a pKa of between 2.3 and 7.3, as described in British Pat. No. 1,097,164 (priority 1965); or by catalytic quantities of sodium methoxide, as described in Portuguese Pat. No. 71,309. The tetrahydrofuran-(2'-yl) ether and the trimethylsilyl ether protecting groups can be removed by acid hydrolysis, whilst the 11-nitrate ester requires zinc in acetic acid.

In respect of the trifluoroacetic group removal, the use of silica or of an alkali or alkaline earth metal salt of an acid with a pKa value of between 2.3 and 7.3, are not methods of choice. This is due to the heterogeneity of the reaction, resulting in a tendency to leave unreacted starting material in the product and thus giving variable results. This problem can also be obtained when sodium bicarbonate is used, since the product and the starting steroid often co-crystallise in the methanolic medium. The use of catalytic quantities of sodium methoxide is the best available prior art method, but here the reaction parameters must be strictly controlled, otherwise ester functions, especially those at the 21-position, can be removed. This is demonstrated in British Pat. No. 1,196,683 (priority 1967) wherein sodium methoxide removes not only an 11-chlorodifluoroacetyl group, but also a 21-acetate group as well.

The other protecting groups present problems in the preparation of derivatives, eliminating them as candidates for viable processes.

The final general method for the preparation of the compounds of the present invention is via the cyclic 17α,21-orthodiesters. This was first described in Belgian Pat. Nos. 618,831 and 619,180 (priorities 1962), and then later described in British Pat. Nos. 1,043,374 and 1,047,518 (priorities 1964). This process, which is only applicable if the starting material has a 17α,21-dihydroxy-20-one sub-structure, works well without the necessity for protection of the 11-hydroxyl. Unfortunately, the acid hydrolysis of the intermediate cyclic orthodiester is not sufficiently selective and is very sensitive to the reaction conditions, yielding in addition to the 17-monoester, the 21-monoester and the 17,21-dihydroxy compounds. Another restraint upon this method is the difficulty of preparation of the starting trialkylorthoesters, those derived from acids with more than six carbon atoms being exceptionally difficult to obtain.

The present invention is based upon the discoveries that the 17-acylation stage can be carried out more simply, more economically in terms of reagents, in better yields and purity than has been hitherto the case, and that the removal of a 11-trifluoroacetate protecting group can be most simply accomplished in almost stoichiometric yield by reaction with either an amine, ammonia or hydrazine.

According to the present invention the starting material, which can be prepared by standard methods known to those skilled in the art, is

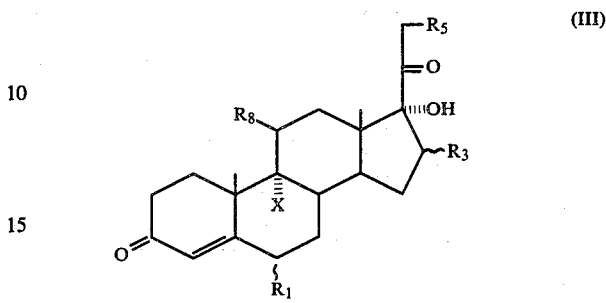

in which $R_8$ is trihaloacetate, oxo or halogen or where $R_8$ and X jointly form an epoxide group. In the case where $R_8$ is trihaloacetate, which is by preference the trifluoroacetate, this protecting group is introduced by standard methods, such as dissolving the 11-hydroxy steroid in pyridine, which can be diluted with a solvent inert for the reaction, such as tetrahydrofuran, and adding trifluoroacetic anhydride, and then isolating the required product by conventional means, such as precipitation in water.

The acylation at the 17-position is carried out with the anhydride of the carboxylic acid, plus a pair of strong acids. The quantity of the anhydride which should be used, is from 1.5 moles per mole of starting steroid upwards. Thus, in the case of the introduction of the 17-valerate group into betamethasone 11-trifluoroacetate 21-acetate (Example 9a), the preferred quantity of valeric anhydride is 0.76 ml/gm. This compares very favourably with the conditions given in British Pat. No. 1,097,165, Example 4, of 10 ml of valeric acid per gm of starting material. One of the pair of strong acids should be a trihaloacetic acid, of which trifluoroacetic acid or trichloroacetic acid are preferred. This acid should also be present in molar quantities above 1.5 in comparison with the starting steroid. Again, in the case of the introduction of the 17-valerate group into betamethasone 11-trifluoroacetate 21-acetate, the preferred quantity of trifluoroacetic acid is 0.58 ml/gm. In comparison, the above mentioned Example 4 in British Pat. No. 1,097,165 uses 4 ml of trifluoroacetic anhydride per gm of starting material.

The second acid of the pair is present in catalytic quantities and can be chosen from a variety of strong acids. Typical of this choice is p-toluenesulphonic acid, methanesulphonic acid, benzenesulphonic acid, perchloric acid and hydrochloric acid.

The order of mixing of the various reagents is not of importance, although it is preferable to cool the reaction vessel during the actual mixing process. Normally, the trihaloacetic acid is cooled to about 0° C., when the acid anhydride is added, followed by the second acid and finally the steroid which is to be reacted.

One of the most surprising features of the present invention, which comprises part of its inventive merit, is that for equivalent quantities of reagents, this new process is considerably faster than that given in the prior art.

The following table refers to the introduction of the 17-valerate into betamethasone 11-trifluoroacetate 21-acetate (see Example 1), comparing the present invention with British Pat. No. 1,097,165. This latter process was later used in U.S. Pat. No. 4,024,131.

The second component of the catalyst in the repetition of the British patent and the process of the present invention was, in both cases, p-toluenesulphonic acid. In the repetition of the British patent, 100 mg/g of betamethasone 11-trifluoroacetate 21-acetate was used, whereas in the process of the present invention only 50 mg/g was used.

TABLE I

| Method | MTFAA/ MSS | MTFA/ MSS | MVA/ MSS | MAVA/ MSS | Reaction temperature | Time to completion by chromatography |
|---|---|---|---|---|---|---|
| British Patent 1,097,165 Example 4 | 14.84 | — | 47.44 | — | 28° C. | 1 hour |
| Half of above conditions | 7.42 | — | 23.72 | — | 28° C. | 3 hours |
| Present Invention | — | 7.61 | — | 3.80 | 28° C. | Less than 1 hour |
| Present Invention | — | 4.00 | — | 2.00 | 28° C. | 1 hour | where
MTFAA/MSS is the molar ratio of trifluoroacetic anhydride to the starting steroid
MTFA/MSS is the molar ratio of trifluoroacetic acid to the starting steroid
MVA/MSS is the molar ratio of valeric acid to the starting steroid
MAVA/MSS is the molar ratio of valeric anhydride to the starting steroid Table I shows that the use of 4 moles of trifluoroacetic acid (a reduction of 3.7 times in comparison with the trifluoroacetic anhydride used in the British patent) and 2 moles of valeric anhydride (a reduction of 23.7 times in comparison with the valeric anhydride used in the British patent) caused complete reaction in one hour. The table shows that halving the quantities of reagents of the prior art tripled the reaction time while in the present invention, the quantities were reduced by 3.7 and 23.7 times while maintaining the same reaction time.

The stoichiometric yield of betamethasone 11-trifluoroacetate 17-valerate 21-acetate in a repetition of the one hour complete reaction shown in Table I was 94.1% for the process of the present invention and the product had a purity of 97.1%. This is equivalent to a stoichiometric pure yield of 86.3%. The stoichiometric yield of the one hour complete reaction of the British Pat. No. 1,097,165 shown in Table I was 76.7% and the product had a purity of 48.9%. This is equivalent to a stoichiometric pure yield of 37.5%. A further experiment carried out exactly as Example 4 of British Pat. No. 1,097,165, including the purification by column chromatography of the crude product, gave a stoichiometric pure yield of betamethasone 11-trifluoroacetate 17-valerate 21-acetate of 40.6%. Accordingly, in addition to the much faster reaction, the process of the invention produced a greater yield of product and the product produced had a greater purity. Two further advantages of the present process are the fact that steam distillation was not required in the work-up of the reaction mixture, and column chromatography was not required due to the much greater product purity.

This increase in the rate of reaction is believed to be due, in part, to the higher dielectric constant of the reaction mixture. This is bourne out by the fact that the use of some inert diluents of relatively low dielectric constant do not allow the reaction to proceed.

Hence, it has been found that esterification occurs in the presence of acetonitrile or nitromethane, whereas in the presence of tetrahydrofuran, dioxan, chloroform and acetone the reaction is extremely slow and even after a 6 hour reaction the majority of the starting steroid is recovered unchanged. It will be noted that the two above mentioned successful diluents have high dielectric constants.

It will be noted that $R_5$ in the starting material compound III can be hydroxyl, so that when symmetrical 17,21-diesters are required, the aforementioned reaction can be carried out on a 17,21-dihydroxy steroid. Once the reaction is complete, the isolation method is dependent upon the starting material and on the desired product. Thus, when $R_8$ in compound III is oxo or halogen or forms an epoxide group jointly with X, the product is obtained by conventional means, such as precipitation in water. This is also a part of the inventive merit of the present invention over the prior art, since the latter teaches that steam distillation is usually required, a process which is not acceptable on an industrial scale. This is to remove the vast excess of acidic or pro-acidic reagents originally used, otherwise precipitation yields an oil, which is often intractable. Thus, the minimal quantities desirable in the present invention not only produce a faster, cleaner reaction, but also facilitate the obtention of the required product. Similarly, when $R_8$ is trihaloacetate, isolation of the product by conventional means, such as precipitation in water, will give the 11-trihaloacetate 17-esterified product. Since the trifluoroacetate group is not pharmaceutically acceptable, it must normally be removed. Thus, a further feature of the present invention is the direct isolation of the 11-hydroxyl compounds, which can be accomplished by the use of amines or ammonia. It has been established that an amine or ammonia, whether in the presence of water or not, will selectively remove an 11-trifluoroacetate group and this will be more fully discussed hereinafter. The substitution pattern of the amine does not seem to be of vital importance. However, those amines in which nitrogen forms part of an aromatic ring, for example pyridine, are inactive and are excluded from the group of useful amines.

It is possible to isolate the required products by two slightly different processes. Thus, the amine can be added to the acylating reaction mixture and the product isolated by conventional means such as precipitation in water. Alternatively, the reaction mixture can be precipitated directly using a water/amine mixture, or using an ammonium hydroxide solution. The quantity of amine or ammonium hydroxide used should be in excess, guaranteeing the neutralisation of the various acidic or pro-acidic constituents of the acylating mixture. In some instances, it is necessary to add, on solubility grounds, an inert diluent, such as dioxan, tetrahydrofuran or dimethylformamide, to ensure that the trifluoroacetate group is completely eliminated. The present invention thus allows the introduction of the ester group(s) required and the subsequent selective removal of the trifluoroacetate protecting group without isolating the intermediate compound, the accomplishment of which has until now required two separate reactions. This is another highly significant aspect of the present invention, that the introduction of the 17-ester or 17- and 21-ester functions and the removal of the pharmaceutically unacceptable 11-trifluoroacetate group can be accomplished in "one-pot" without the isolation of any intermediate. Example 13 shows dexamethasone dipropionate being produced by esterification and then direct removal of the 11-trifluoroacetate group in a stoichiometric yield of 88.5% with the melting point being unchanged upon recrystallisation. Similarly, the stoichiometric yield of 21-desoxybetamethasone 17-heptanoate in Example 2 is 91.7%. Before the present invention, esterification and deblocking without isolation of the intermediate has not been possible.

The direct precipitation of an 11-trifluoroacetyl 17-esterified steroid was discussed above, and in order to obtain the 11-hydroxyl product, it is necessary to remove the trifluoroacetate group. It has been found that the use of an amine, ammonia or hydrazine, whether in the presence of water or not, can accomplish this in almost stoichiometric yield. The steroid is dissolved in a lower alcohol, preferably methanol or ethanol, plus an inert diluent, such as tetrahydrofuran, dioxan, dimethylformamide, if so required. The amine is then added in small quantities, preferably between 0.01 and 1.0 mole per mole of the starting material. The reaction is normally complete in about fifteen minutes at room temperature. The product can be isolated by conventional means, such as precipitation in water. Alternatively, a solution of ammonia gas in an absolute lower alcohol can be used instead of the amine.

The use of hydrazine is limited to those compounds in which $R_5$ of formula I is hydrogen, halogen or two halogen substituents. Apart from this, the reaction proceeds in the same manner as for the amines. Hydrazine is less applicable than amines or ammonia in the case where $R_5$ in formula I is an acyl group, occasionally provoking the formation of by-products.

As is well known to those skilled in the art, corticosteroid 17-monoesters are particularly active. It is a further inventive feature of the present process that the 11-trifluoroacetate group can be removed from the 11-trifluoroacetyl-17-ester-21-hydroxy steroids, utilizing an amine or ammonia. The trifluoroacetate group surprisingly exerts a stabilising effect on the 17-ester function, in that none or negligible quantities of the 21-ester are obtained during the removal of the trifluoroacetate group, it being well known that this transesterification reaction is facile under both acidic or basic conditions. These 11,17-diesters can be best prepared from compound III in which $R_5$ is either $OR_7$ or hydroxyl by the above process of acylation, followed by strong acid solvolysis, as is fully discussed in Portuguese Patent No. 71,309.

Another example of the surprising stabilising effect of the 11-trifluoroacetate group on the 17-ester function is that the 11-trifluoroacetyl-17α,21-orthodiesters can be successfully hydrolysed in the presence of aqueous amines or ammonia, affording primarily the 17-esterified product. Under precisely the same conditions, 11-hydroxy-17α,21-orthodiesters are recovered unchanged from the reaction.

The compounds of the present invention were tested according to a modified McKenzie vasoconstriction test. Creams, prepared using the formulation given in Example 30, were applied to the backs of healthy volunteers. The occlusive tape, covering the sterile gauze used for the application, was removed after 16 hours and the areas viewed at time intervals up to six hours. Betamethasone 17-valerate was used as the control, and surprisingly it was found that several of the previously unknown steroids showed excellent topical activity. As can be seen from the table in Example 30 the experimentally found activities were higher than the control, especially those containing a 16α-methyl group.

The products of the present invention when mixed with pharmaceutically acceptable excipients and diluents, well known to those skilled in the art, are active in locally applied topical formulations. Typical of these formulations are creams, ointments, lotions, eye-drops and oral inhalation sprays. The content of the active principle depends on the actual formulation, but are generally between 0.001% w/w and 0.5% w/w, more preferably between 0.01% w/w and 0.25% w/w.

The formulations prepared with the products of the present invention can be used in the topical management of corticosteroid-responsive dermatoses, which may include
Psoriasis
Eczemas
Neurodermatitis
Seborrhoeic dermatitis
Contact dermatitis
Atopic dermatitis
Intertrigo In addition, the 21-desoxybetamethasone 17-heptanoate prepared in Example 2 is especially suitable for use as a long-acting active principle in an intramuscular injection.

Certain compounds which can be made by the process of the invention are novel per se and form a further aspect of the present invention. These include:
9α-Chloro-17α-hydroxy-16β-methylpregna-1,4-diene-3,11,20-trione 17-butyrate;
9α-Chloro-11β,17α,21-trihydroxy-16β-methylpregna-1,4-diene-3,20-dione 17-acetate;
9α-Chloro-11β,17α,21-trihydroxy-16β-methylpregn-4-ene-3,20-dione 17,21-dipropionate;
9α-Fluoro-11β,17α,21-trihydroxy-16α-methylpregna-1,4-diene-3,20-dione 17-butyrate 21-acetate;
9α-Fluoro-11β,17α,21-trihydroxy-16α-methylpregna-1,4-diene-3,20-dione 17-isobutyrate 21-acetate.

The invention further includes pharmaceutical compositions which comprises a novel compound of the invention or a compound made by the process of the invention, and an inert pharmaceutically acceptable carrier therefor.

The following examples serve to illustrate the present invention, without in any way limiting the scope thereof.

EXAMPLE 1

PREPARATION OF BETAMETHASONE 11-TRIFLUOROACETATE 17-VALERATE 21-ACETATE

Four experiments were carried out to illustrate the fact that the acylation conditions of the present invention are faster than those of the prior art. The first experiment used the conditions of British Pat. No. 1,097,165, Example 4, whilst the second used twice the amount of starting betamethasone 11-trifluoroacetate 21-acetate as was present in the first experiment. The other two trials used conditions from the present invention. Samples were removed at timed intervals and diluted with water, then chloroform extracted, which was washed with water and dried by passage through anhydrous sodium sulphate. The course of each reaction was monitored by thin layer chromatography, and the results are given in Table I above. These clearly indicated that the reaction is complete in a shorter time with considerably less reagents present when the process of the present invention is employed.

EXAMPLE 2

PREPARATION OF 21-DESOXYBETAMETHASONE 17-HEPTANOATE

Heptanoic anhydride (8.40 ml; 31.78 mmoles) and trichloroacetic acid (5.20 g; 31.82 mmoles) were mixed at 0° C., after which p-toluenesulphonic acid (0.50 g) and 9α-fluoro-11β,17α-dihydroxy-16β-methylpregna-1,4-diene-3,20-dione 11-trifluoroacetate (10.00 g; 21.16 mmoles) were added. The mixture was stirred at 40°-45° C. for 4 hours, cooled to ambient temperature, and then poured into 50% aqueous isopropylamine. The precipitated solid was filtered, well washed with water, and dried at 50° C. to give 9.48 g of 21-desoxybetamethasone 17-heptanoate. Recrystallisation from methanol gave an analytically pure material, with the following characteristics: melting point 194°-6° C. and specific rotation in dioxan +54.28°.

EXAMPLE 3

PREPARATION OF DEXAMETHASONE 17-VALERATE 21-ACETATE

Valeric anhydride (3.90 ml; 19.47 mmoles) was added to previously cooled trifluoroacetic acid (1.50 ml; 19.60 mmoles), followed by benzenesulphonic acid (250 mg) and finally 9α-fluoro-11β,17α,21-trihydroxy-16α-methylpregna-1,4-diene-3,20-dione 11-trifluoroacetate 21-acetate (5.00 g; 9.68 mmoles). The mixture was stirred at 40°-45° C. for two hours, before 25% ammonium hydroxide was added. After stirring for 30 minutes, the mixture was poured into ice cold water and the precipitated solid collected by filtration, washed with water and dried at 50° C. The product, which weighed 4.80 g, was shown to be chromatographically identical with an authentic sample of the title compound. The recrystallised product had a melting point of 159° C.

EXAMPLE 4

PREPARATION OF BECLOMETHASONE 17,21-DIACETATE

Acetic anhydride (2.00 ml; 21.16 mmoles), trifluoroacetic acid (2.00 ml; 26.13 mmoles) and p-toluenesulphonic acid (0.25 g) were mixed at 0° C., and 9α-chloro-11β,17α,21-trihydroxy-16β-methylpregna-1,4-diene-3,20 dione 11-trifluoroacetate (2.50 g; 4.95 mmoles) was added. The mixture was stirred at 40° C. for 1 hour 35 minutes, then cooled to 0° C. and tetrahydrofuran (10 ml) and 12.5% aqueous ammonia (25 ml) added. After stirring for 30 minutes, the mixture was poured into ice cold water. The precipitated product was filtered, washed with water, dried at 50° C. to yield 2.27 g of the above compound. An analytical sample was obtained by recrystallisation from methanol and had the following analytical values: melting point 228°-231° C. and specific rotation in chloroform of +87.28°.

EXAMPLE 5

PREPARATION OF 9α,11β-DICHLORO-17α,21-DIHYDROXY-16β-METHYLPREGNA-1,4-DIENE-3,20-DIONE 17-VALERATE 21-ACETATE

Trifluoroacetic acid (4.80 ml; 62.72 mmoles), valeric anhydride (4.80 ml; 23.97 mmoles) and methanesulphonic acid (0.400 ml) were mixed at 0° C. and then 9α,11β-dichloro-17α,21-dihydroxy-16β-methylpregna-1,4-diene-3,20-dione 21-acetate (7.50 g; 15.98 mmoles) was added. The mixture was stirred at 40° C. for 2 hours, then poured slowly into ice cold water. Collection of the precipitate by filtration, washing with water and drying at 50° C. yielded 8.90 g of the title compound. Recrystallisation from methanol gave an analytically pure sample with specific rotation in dioxan of +110.53°. The CI mass spectrum exhibited a typical molecular ion pattern centred on m/e 553 (M+1), with the base peak at m/e 323.

EXAMPLE 6

PREPARATION OF 21-DESOXYBECLOMETHASONE 17-BUTYRATE

Butyric anhydride (5.25 ml; 32.19 mmoles), trifluoroacetic acid (5.25 ml; 68.60 mmoles) and methanesulphonic acid (0.45 ml) were mixed at 0° C., and then 9α-chloro-11β,17α-dihydroxy-16β-methylpregna-1,4-diene-3,20-dione 11-trifluoroacetate (7.50 g; 15.34 mmoles) was added. The reaction mixture was stirred at 40° C. for 2 hours 30 minutes, and then poured into a mixture of tetrahydrofuran (17.4 ml) and 12.5% aqueous ammonia (43.5 ml). After stirring for 15 minutes, the mixture was poured into ice cold water, the product filtered, washed with water and dried at 50° C. to yield 6.29 g of the title compound. After washing with an ice-cold methanol and acetone mixture, the product had the following analytical values: melting point 238°-240° C. and specific rotation in chloroform +102.72°.

EXAMPLE 7

PREPARATION OF 9α-CHLORO-17α-HYDROXY-16β-METHYL-PREGNA-1,4-DIENE-3,11,20-TRIONE 17-BUTYRATE

9α-Chloro-17α-hydroxy-16β-methylpregna-1,4-diene-3,11,20-trione can be prepared from the respective 11β-hydroxy compound by oxidation with Cornforth reagent in pyridine, followed by precipitation in water. The use of trifluoroacetic acid (3.50 ml; 45.73 mmoles), butyric anhydride (3.20 ml; 19.62 mmoles), methanesulphonic acid (0.25 ml) with this starting material (5.00 g; 12.79 mmoles) in the normal fashion at 40° C. for 2 hours, yielded, after precipitation in water and recrystallisation from methanol:dichloromethane:di-isopropyl ether, 5.27 g of the title compound. The melting point was 154°-5° C. and the specific rotation in chloroform was +198.83°.

EXAMPLE 8

PREPARATION OF 9α,11β-DICHLORO-17α-HYDROXY-16β-METHYLPREGNA-1,4-DIENE-3,20-DIONE 17-VALERATE

Valeric anhydride (4.80 ml; 23.97 mmoles) was added to cooled trifluoroacetic acid (4.80 ml; 62.72 mmoles) followed by methanesulphonic acid (0.400 ml) and finally 9α,11β-dichloro-17α-hydroxy-16β-methylpregna-1,4-diene-3,20-dione (7.50 g; 18.23 mmoles). The temperature was raised to 40° C. and the mixture stirred for 1 hour 45 minutes, and then poured slowly into ice cold water. The solid so obtained was filtered, washed with water, vacuum dried over potassium hydroxide pellets and immediately recrystallised from methanol to yield 6.97 g of the title compound. Further product could be obtained by concentration of the mother liquors. The melting point was 170°-2° C. and specific rotation in dioxan was +118.54°.

EXAMPLE 9

PREPARATION OF BETAMETHASONE 17-VALERATE 21-ACETATE (a) Trifluoroacetic acid (31.32 ml; 0.409 moles), valeric anhydride (41.04 ml; 0.205 moles) and p-toluenesulphonic acid (2.70 g) were mixed at 0° C. and 9α-fluoro-11β,17α,21-trihydroxy-16β-methylpregna-1,4-diene-3,20-dione 11-trifluoroacetate 21-acetate (54.00 g; 0.102 mmoles) was then added. The temperature was raised to 40° C. and the mixture stirred efficiently for 1 hour 25 minutes. Treatment with an ice-cold 10% pyridine:water mixture, followed by dissolution of the oily solid in methanol and precipitation in ice cold water gave a crystalline product, which was filtered, washed with water and dried at 50° C. The yield of betamethasone 11-trifluoroacetate 17-valerate 21-acetate was 60.10 g, the product having and $E_1\ cm^{1\%}$ in methanol of 242 at 235-7 nm.

(b) The betamethasone 11-trifluoroacetate 17-valerate 21-acetate can then be transformed into betamethasone 17-valerate 21-acetate by the following general process:

The starting material was mixed with the chosen reagent in the solvent and stirred at the given temperature for the specified time. The product was obtained by precipitation in ice cold water, filtration, water washing, and drying at 50° C.

The results of various experiments are given in Table II.

EXAMPLE 10

PREPARATION OF BETAMETHASONE 17-VALERATE (a) According to Portuguese Pat. No. 71,309, Example 1, 9α-fluoro-11β,17α,21-trihydroxy-16β-methylpregna-1,4-diene-3,20-dione 11-trifluoroacetate 17-valerate 21-acetate (45.00 g) prepared as in Example 9a, methanesulphonic acid (2.25 ml) and absolute methanol (135 ml) were stirred, with the exclusion of moisture, for 45 hours at 18° C. and then 23.5 hours at between 18° C. and 25° C. The mixture was poured into ice cold water, and the precipitated solid filtered, well washed with water, and dried at 50° C. to yield 38.50 g of betamethasone 11-trifluoroacetate 17-valerate. Recrystallisation from hot aqueous methanol gave an analytical sample with a melting point of 174°-177° C.

(b) The betamethasone 11-trifluoroacetate 17-valerate can then be transformed into betamethasone 17-valerate by the following general process:

The starting material was mixed with the chosen reagent in absolute methanol and stirred at the given temperature for the specified time.

TABLE II

| Betamethasone 11-trifluoroacetate 17-valerate 21-acetate | | Chosen Reagent | Reagent | | Absolute Methanol | Water | Time | Temperature | Yield | Melting Point |
|---|---|---|---|---|---|---|---|---|---|---|
| g | mmoles | | ml | mmoles | ml | ml | minutes | °C. | g | °C. |
| 2.00 | 3.25 | Cyclohexylamine | 0.05 | 0.44 | 12 | — | 15 | 22 | 1.55 | 204 |
| 2.00 | 3.25 | Benzylamine | 0.04 | 0.37 | 12 | — | 15 | 21 | 1.53 | 197-200 |
| 2.00 | 3.25 | Diethylamine | 0.05 | 0.48 | 12 | — | 20 | 23 | 1.55 | 202-208 |
| 1.00 | 1.63 | Piperidine | 0.002 | 0.02 | 6 | — | 2.5 days | 28 | 0.78 | 204-205 |
| 5.00 | 8.13 | Triethylamine | 0.50 | 3.58 | 25 | — | 20 | 10 | 4.02 | 203-4 |
| 2.00 | 3.25 | Ammonia in Absolute Methanol | 6.8 | 2.33 | 5.2 | — | 30 | 21 | 1.56 | 203-4 |
| 2.00 | 3.25 | Triethylamine | 0.20 | 1.43 | 12 | 0.20 | 30 | 24 | 1.59 | 198-9 |

The product was obtained by precipitation in ice cold water, filtration, water washing and drying at 50° C.

The results of various experiments are given in Table III.

EXAMPLE 11

PREPARATION OF 9α-FLUORO-11β,17α-DIHYDROXY-21,21-DIIODO-16β-METHYLPREGNA-1,4-DIENE-3,20-DIONE 17-VALERATE (a) Valeric anhydride (15.03 ml; 75.05 mmoles) and trifluoroacetic acid (13.20 ml; 172.48 mmoles) were mixed at 0° C., then methanesulphonic acid (1.25 ml) followed by 9α-fluoro-11β,17α-dihydroxy-21,21-diiodo-16β-methylpregna-1,4-diene-3,20-dione 11-trifluoroacetate (25.00 g; 34.52 mmoles) were added. After stirring for two hours, the reaction mixture was poured slowly into a 0.025M disodium hydrogen phosphate solution. The aqueous phase was decanted off, and the residue dissolved in 50% acetone:methanol. After precipitation in ice cold water, the product was filtered, washed well with water, and dried at 35° C. to yield 27.55 g. An analytical sample of this unstable product was obtained from aqueous methanol in the presence of a small amount of p-toluenesulphonic acid. The iodine content was found to be 28.5%.

(b) The above product (3.00 g) was dissolved in methanol (18 ml) and triethylamine (3 ml; 21.54 mmoles) was added, after which the mixture was stirred for 30 minutes at room temperature. Precipitation in ice cold water yielded the title compound, which was filtered, washed with water and dried at 35° C. The iodine content was shown to be 23.7%.

EXAMPLE 12

PREPARATION OF 21-DESOXYBETAMETHASONE 17-VALERATE (a) Trichloroacetic acid (2.60 g; 15.91 mmoles) and valeric anhydride (3.18 ml; 15.88 mmoles) were mixed at 0° C., then p-toluenesulphonic acid (250 mg) was added, followed by 9α-fluoro-11β,17α-dihydroxy-16β-methylpregna-1,4-diene-3,20-dione 11-trifluoroacetate (5.00 g; 10.58 mmoles). The mixture was warmed to 40° C. and maintained at this temperature for 4 hours. After cooling to ambient temperature, triethylamine (25 ml) was added and stirring continued for a further 30 minutes. Precipitation with ice cold water gave a solid, which was filtered, washed with water and dried at 50° C. Recrystallisation from methanol gave an analytical sample with a melting point of 216°–8° C., and a rotation in dioxan of +62.17°.

This melting point was unchanged on recrystallisation from aqueous methanol.

EXAMPLE 14

PREPARATION OF BECLOMETHASONE 17-ACETATE (a) Triethylamine (0.200 ml; 1.43 mmoles) was added to a solution of 9α-chloro-11β-hydroxy-16β-methyl-17α,21(1'-methyl-1'-methoxy)methylenedioxy-pregna-1,4-diene-3,20-dione 11-trifluoroacetate (2.00 g; 3.56 mmoles) in methanol (8 ml), tetrahydrofuran (8 ml) and water (2 ml). After stirring overnight the mixture was poured into ice cold water, the product filtered, washed with water and dried at 50° C. to yield 1.50 g of the title product. Recrystallisation from methanol gave a compound with a melting point of 221°–223° C. and a specific rotation in dioxan of +106.36°.

(b) When the reaction mixture in Example 4 was precipitated in water, without prior treatment with ammonia, beclomethasone 11-trifluoroacetate 17,21-diacetate was obtained. This was reacted with anhydrous methanesulphonic acid in absolute methanol, by the process given in Portuguese Patent No. 71,309, to yield beclomethasone 11-trifluoroacetate 17-acetate, which was further treated with an amine to give beclomethasone 17-acetate. Recrystallisation from methanol gave an analytical sample with a specific rotation in dioxan of +106.58°.

TABLE III

| Betamethasone 11-trifluoroacetate 17-valerate | | Chosen | Reagent | | Absolute Methanol | Water | Time | Temperature | Yield | Melting Point |
|---|---|---|---|---|---|---|---|---|---|---|
| g | mmoles | Reagent | ml | mmoles | ml | ml | minutes | °C. | g | °C. |
| 2.00 | 3.49 | Ethylamine | 0.05 | 0.76 | 12 | — | 20 | 25 | 1.60 | 183–8 |
| 2.00 | 3.49 | Butylamine | 0.04 | 0.40 | 12 | — | 20 | 22 | 1.59 | 186–8 |
| 2.00 | 3.49 | Ethylenediamine | 0.10 | 1.49 | 12 | — | 30 | 21 | 1.67 | 192 |
| 2.00 | 3.49 | Morpholine | 0.20 | 2.31 | 12 | — | 20 | 21 | 1.56 | 193–4 |
| 2.00 | 3.49 | Pyrrolidine | 0.05 | 0.60 | 12 | — | 20 | 22 | 1.60 | 185–7 |
| 2.00 | 3.49 | Triethanolamine | 0.04 | 0.30 | 12 | — | 30 | 21 | 1.57 | 193 |
| 2.00 | 3.49 | Ammonia in Absolute Methanol | 6.8 | 2.33 | 5.2 | — | 20 | 22 | 1.53 | 192–4 |
| 2.00 | 3.49 | Ammonium Hydroxide | 0.10 | 1.47 | 12 | — | 15 | 28 | 1.65 | 196 |
| 2.00 | 3.49 | Isopropylamine | 0.10 | 1.17 | 12 | 0.10 | 15 | 28 | 1.70 | 198–91 |

(b) When the reaction above is not treated with triethylamine, but merely precipitated in water, 21-desoxybetamethasone 11-trifluoroacetate 17-valerate is obtained.

(c) 9α-Fluoro-11β,17α-dihydroxy-16β-methylpregna-1,4-diene-3,20-dione 11-trifluoroacetate 17-valerate (2.00 g; 3.59 mmoles) in absolute methanol (24 ml) was treated with 100% hydrazine (0.400 ml; 12.52 mmoles) for 15 minutes at 24° C. The reaction mixture was poured into ice cold water, and the product filtered, washed and dried to yield 1.56 g of the title compound, having a melting point of 212°–5° C.

EXAMPLE 13

PREPARATION OF DEXAMETHASONE 17,21-DIPROPIONATE

Trifluoroacetic acid (2.11 ml; 27.57 mmoles) was cooled to 0° C., and propionic anhydride (2.37 ml; 18.39 mmoles) was added, followed by methanesulphonic acid (0.25 ml) and 9α-fluoro-11β,17α,21-trihydroxy-16α-methylpregna-1,4-diene-3,20-dione 11-trifluoroacetate 21-propionate (5.00 g; 9.18 mmoles). After stirring at 40°–45° C. for 1 hour, the mixture was poured into a 50% aqueous solution of diethylamine. Filtration, washing and drying at 50° C. gave 4.10 g of dexamethasone 17,21-dipropionate, with a melting point of 204°–6° C.

EXAMPLE 15

PREPARATION OF BECLOMETHASONE 17,21-DIPROPIONATE (a) Trifluoroacetic acid (1.20 ml; 15.68 mmoles) was cooled at 0° C., when propionic anhydride (1.512 ml; 11.73 mmoles) was added, followed by methanesulphonic acid (0.20 ml) and 9α-chloro-11β,17α,21-trihydroxy-16β-methylpregna-1,4-diene-3,20-dione 11-trifluoroacetate 21-propionate (4.00 g; 7.13 mmoles). The mixture was heated to 80° C. and maintained at this temperature for 2.5 hours, with stirring. After precipitation with ice cold water, the product was filtered, washed well with water, and dried at 50° C. to yield 4.02 g of beclomethasone 11-trifluoroacetate 17,21-dipropionate. Recrystallisation from methanol gave an analytically pure sample with a melting point of 176°–7° C.

(b) 9α-Chloro-11β,17α,21-trihydroxy-16β-methylpregna-1,4-diene-3,20-dione 11-trifluoroacetate 17,21-dipropionate (3.00 g; 4.86 mmoles) was dissolved in methanol (18 ml) and dioxan (12 ml), after which morpholine (0.300 ml; 3.48 mmoles) was added. After stirring at 25° C. for 1 hour, the reaction mixture was neutralised with 50% aqueous acetic acid, and precipitated in ice cold water. Filtration, washing with water and drying at 50° C. gave 2.45 g of beclomethasone 17,21-dipropionate. After a recrystallisation from acetone, the product complied with the United States Pharmacopoeia XX hplc assay for this product.

and had a melting point of 200° C. and specific rotation in dioxan of +99.21°.

(c) The product obtained in stage (a) above (100 mg; 0.18 mmoles) was suspended in absolute methanol. After adding 100% hydrazine (100 μl; 3.13 mmoles), the mixture was stirred at 28° C. for 15 minutes, and then precipitated in ice cold water. The product was shown to be chromatographically identical with that obtained in stage (b) above.

TABLE IV

| 21-Desoxybeclomethasone 11-trifluoroacetate 17-valerate | | Chosen Reagent | Reagent | | Absolute Methanol ml | Water ml | Time minutes | Temperature °C. | Yield g | Melting Point °C. |
|---|---|---|---|---|---|---|---|---|---|---|
| g | mmoles | | ml | mmoles | | | | | | |
| 2.00 | 3.49 | Butylamine | 0.04 | 0.40 | 12 | — | 15 | 21 | 1.62 | 239–41 |
| 2.00 | 3.49 | Diethylamine | 0.10 | 0.97 | 12 | — | 15 | 21 | 1.61 | 239–40 |
| 2.00 | 3.49 | Triethylamine | 0.2 | 1.43 | 12 | — | 120 | 21 | 1.60 | 240–42 |
| 2.00 | 3.49 | Pyrrolidine | 0.20 | 2.40 | 12 | 0.2 | 15 | 21 | 1.60 | 240 |

EXAMPLE 16

PREPARATION OF 21-DESOXYBECLOMETHASONE 17-VALERATE (a) A mixture of trifluoroacetic acid (17.00 ml; 353 mmoles) and valeric anhydride (13.50 ml; 67.4 mmoles) was prepared at 0° C., after which p-toluenesulphonic acid (1.80 g) and 9α-chloro-11β,17α-dihydroxy-16β-methylpregna-1,4-diene-3,20-dione 11-trifluoroacetate (18.00 g; 36.8 mmoles) were added. The temperature was raised to 40° C. and the reaction stirred for 2 hours. Precipitation with ice cold water gave an oily solid, which crystallised when triturated with methanol. Filtration and drying at 50° C. gave 17.71 g of 21-desoxybeclomethasone 11-trifluoroacetate 17-valerate, with a melting point of 187°–90° C.

(b) The above product was then transformed into 21-desoxybeclomethasone 17-valerate by the following procedure:

The starting material was mixed with the chosen reagent in the solvent and stirred at the given temperature for the specified time. The product was obtained by precipitation in ice cold water, filtration, water washing and drying at 50° C.

The results of some experiments are given in Table IV.

EXAMPLE 17

PREPARATION OF CLOBETASOL 17-PROPIONATE (a) Trifluoroacetic acid (2.23 ml; 29.14 mmoles) and propionic anhydride (2.50 ml; 19.40 mmoles) were mixed at 0° C., after which 70% perchloric acid (0.272 ml) and 21-chloro-9α-fluoro-11β,17α-dihydroxy-16β-methylpregna-1,4-diene-3,20-dione 11-trifluoroacetate (4.90 g; 9.67 mmoles) were added. Stirring at 40°–45° C. for 3 hours and precipitation in ice cold water, gave a solid, which was filtered, washed well with water and dried at 50° C. The product, clobetasol 11-trifluoroacetate 17-propionate, weighed 5.15 g.

(b) The product obtained above (4.78 g) was suspended in methanol (28.7 ml) and triethylamine (1.195 ml; 8.58 mmoles) was added. The mixture was stirred at 25° C. for 30 minutes and then neutralised by the addition of 50% aqueous acetic acid. After precipitation, the product was filtered, washed and dried at 50° C. to yield 3.72 g. An analytical sample of the clobetasol propionate was obtained by recrystallisation from methanol

EXAMPLE 18

PREPARATION OF CLOBETASONE 17-BUTYRATE

Butyric anhydride (5.28 ml; 32.37 mmoles), trifluoroacetic acid (2.376 ml; 31.05 mmoles) were mixed at 0° C., then methanesulphonic acid (0.200 ml), nitromethane (20.0 ml) and 21-chloro-9α-fluoro-17α-hydroxy-16β-methylpregna-1,4-diene-3,11,20-trione (4.00 g; 9.78 mmoles) were added. The reaction mixture was stirred at 40° C. for 3 hours and then poured slowly into ice cold water, to give an oily solid, which was filtered, water washed and dried to yield 3.71 g. Recrystallisation from methanol gave an analytical sample with a melting point of 184°–6° C. and a specific rotation in dioxan of +127.98°.

EXAMPLE 19

PREPARATION OF BETAMETHASONE 17-BENZOATE

9α-Fluoro-11β-hydroxy-16β-methyl-17α,21(1'-phenyl-1'-methoxy)methylenedioxy-pregna-1,4-diene-3,20-dione 11-trifluoroacetate (3.00 g; 4.94 mmoles) was dissolved in a mixture of methanol (12 ml), tetrahydrofuran (12 ml) and water (3 ml), then triethylamine (0.300 ml; 2.15 mmoles) was added. After stirring overnight, the product was obtained by precipitation in ice cold water, followed by filtration, washing and drying at 50° C. The yield of the title compound was 2.55 g. Recrystallisation from methanol gave an analytical pure sample with a melting point of 225° C. and $E_{1cm}^{1\%}$ of 555 at 233–234 nm.

EXAMPLE 20

PREPARATION OF PREDNISOLONE 17-VALERATE 21-ACETATE (a) Valeric anhydride (3.50 ml; 17.48 mmoles) was mixed with trifluoroacetic acid (2.30 ml; 30.05 mmoles) at 0° C., after which methanesulphonic acid (0.25 ml) and 11β,17α,21-trihydroxy-pregna-1,4-diene-3,20-dione 11-trifluoroacetate 21-acetate (5.00 g; 10.03 mmoles) were added. The reaction was warmed to 25° C., stirred for one hour, poured into ice cold water, to give an oily solid. This was dissolved in methanol and precipitated in water to give a solid, which was filtered, washed and dried, yielding 5.30 g of prednisolone 11-trifluoroacetate 17-valerate 21-acetate.

(b) The above product (3.00 g; 5.15 mmoles) in absolute methanol (18 ml) was treated with triethylamine (2.40 ml; 17.21 mmoles) at 24° C. for 5 hours. The product, which was obtained by precipitation in ice cold water, filtration and drying, weighed 2.35 g, and had an $E_{1cm}^{1\%}$ of 279 at 241–3 nm in methanol.

EXAMPLE 21

PREPARATION OF 9α-CHLORO-11β,17α,21-TRIHYDROXY-16β-METHYLPREGN-4-ENE-3,20-DIONE 17,21-DIPROPIONATE

The above product was prepared from 9α-chloro-11β,17α,21-trihydroxy-16β-methylpregn-4-ene-3,20-dione 11-trifluoroacetate 21-propionate by the method given for beclomethasone 17,21-dipropionate under Example 15.

EXAMPLE 22

PREPARATION OF 6α-METHYLPREDNISOLONE 17-BUTYRATE 21-ACETATE

This was prepared in an analogous manner to that of 21-desoxybeclomethasone 17-butyrate in Example 6, starting from 6α-methylprednisolone 11-trifluoroacetate 21-acetate.

EXAMPLE 23

PREPARATION OF DEXAMETHASONE 17-ISOBUTYRATE 21-ACETATE (a) Trifluoroacetic acid (3.75 ml; 49.00 mmoles) and isobutyric anhydride (7.50 ml; 45.18 mmoles) were mixed at 0° C., after which methanesulphonic acid (0.375 ml) and 9α-fluoro-11β,17α,21-trihydroxy-16α-methylpregna-1,4-diene-3,20-dione 11-trifluoroacetate 21-acetate (7.50 g; 14.14 mmoles) were added. The resulting mixture was heated to 60° C., stirred for 3 hours, and then poured into ice cold water. The precipitated solid was filtered, washed with water and dried at 50° C. The product, dexamethasone 11-trifluoroacetate 17-isobutyrate 21-acetate, weighed 8.80 g and had a specific rotation in dioxan of +52.68°.

(b) The product obtained above (7.00 g; 11.65 mmoles) was dissolved in absolute methanol (35 ml) and triethylamine (0.7 ml; 5.02 mmoles). The mixture was stirred at 25° C. for 1 hour and then poured into ice cold water. The title compound, which was obtained by filtering, water washing and drying, weighed 5.70 g. An analytical sample of the product was obtained by recrystallisation from methanol and had a melting point of 196°–7° C. and a specific rotation in dioxan of +29.73°.

EXAMPLE 24

PREPARATION OF DEXAMETHASONE 17-BUTYRATE 21-ACETATE

This was prepared using the same conditions as Example 23, except for the use of butyric anhydride instead of isobutyric anhydride. The title compound had a melting point of 173°–5° C. and a specific rotation in dioxan of +26.65°.

EXAMPLE 25

PREPARATION OF 21-DESOXYDEXAMETHASONE 17-PROPIONATE

This was prepared using 9α-fluoro-11β,17α-dihydroxy-16α-methylpregna-3,20-dione 11β-trifluoroacetate and propionic anhydride by the method given in Example 2. The title compound had a $E_{1cm}^{1\%}$ of 358 at 238–9 nm in methanol.

EXAMPLE 26

PREPARATION OF 21-DESOXYDEXAMETHASONE 17-BUTYRATE

This was prepared according to Example 25, using butyric anhydride, and the product had a melting point of 190°–2° C.

EXAMPLE 27

PREPARATION OF 21-DESOXYDEXAMETHASONE 17-ISOBUTYRATE

This was prepared according to Example 25, using isobutyric anhydride, and the product had an $E_{1cm}^{1\%}$ of 326 at 236–7 nm in methanol.

EXAMPLE 28

PREPARATION OF 9,11-EPOXY-17α,21-DIHYDROXY-16α-METHYLPREGNA-1,4-DIENE-3,20-DIONE 17,21-DIPROPIONATE

The process of Example 13 was applied to 9,11-epoxy-17α,21-dihydroxy-16α-methylpregna-1,4-diene-3,20-dione 17,21-dipropionate to yield the title compound, which after recrystallisation had a melting point of 176° C.

EXAMPLE 29

COMPARATIVE VASOCONSTRICTION ACTIVITIES

The procedure used was that developed by McKenzie and Stoughton (Arch. Derm. 86, 608–10, (1962)), modified by the work Ishihara (Nishinihon J. Derm 37, 86, (1975)). Thus, creams of each of the steroids to be tested were prepared at concentrations of 0.1%, 0.05% and 0.0125%. Aliquots (50 mg) of the creams were applied to the backs of healthy individuals, and covered with sterile gauze and occlusive tape. The tape was removed after 16 hours, and the area of application cleaned with a mild soap/water mixture. Each individual application area was visually estimated for up to six hours. Statistical treatment of the readings has given the following table of results:

| Compound | Vasoconstrictor activity (taking Fluocinolone Acetonide as 100) |
|---|---|
| 9α-Fluoro-11β,17α,21-trihydroxy-16β-methyl-pregna-1,4-diene-3,20-dione 17-valerate | 360 |
| 9α-Chloro-17α-hydroxy-16β-methylpregna-1,4-diene-3,11,20-trione 17-butyrate | 390 |
| 9α-Chloro-11β,17α,21-trihydroxy-16β-methyl-pregna-1,4-diene-3,20-dione 17-acetate | 410 |
| 9α-Chloro-11β,17α,21-trihydroxy-16β-methyl-pregn-4-ene-3,20-dione 17,21-dipropionate | 540 |
| 9α-Fluoro-11β,17α,21-trihydroxy-16α-methyl- | 1190 |

-continued

| Compound | Vasoconstrictor activity (taking Fluocinolone Acetonide as 100) |
|---|---|
| pregna-1,4-diene-3,20-dione 17-butyrate 21-acetate | |
| 9α-Fluoro-11β,17α,21-trihydroxy-16α-methyl-pregna-1,4-diene-3,20-dione 17-isobutyrate 21-acetate | 1280 |
| 9α-Fluoro-11β,17α-dihydroxy-16α-methyl-pregna-1,4-diene-3,20-dione 17-propionate | 1390 |
| 9α-Fluoro-11β,17α-dihydroxy-16α-methyl-pregna-1,4-diene-3,20-dione 17-butyrate | 380 |
| 9α-Fluoro-11β,17α-dihydroxy-16α-methyl-pregna-1,4-diene-3,20-dione 17-isobutyrate | 270 |
| 9α-Fluoro-11β,17α,21-trihydroxy-16α-methyl-pregna-1,4-diene-3,20-dione 17,21-dipropionate | 1145 |

EXAMPLE 30

WATER MISCIBLE CREAM FORMULATION

A water miscible cream of clobetasol 17-propionate can be prepared as follows:

| Part I - The following are mixed and melted at 70° C.: | |
|---|---|
| Cetostearyl alcohol ("Lanette O" ®) | 18.0% |
| Cetostearyl alcohol containing approximately 12 moles of ethylene oxide ("Eumulgin B1" ®) | 1.5% |
| Cetostearyl alcohol containing approximately 20 moles ethylene oxide ("Eumulgin B2" ®) | 1.5% |
| Caprylic/capric acid triglyceride ("Myritol 318") | 10.0% |
| Part II - Suspend at room temperature: | |
| Clobetasol 17-propionate | the equivalent to 0.05% of clobetasol |
| Glycerol and ball mill it. | 5.0% |
| Part III - Dissolve at boiling point: | |
| Methyl 4-hydroxybenzoate in | 0.3% |
| Bidistilled water | 63.65% |
| Cool to 70° C. and adjust volume, if necessary. | |

One third of Part III is added to Part I with stirring at 70° C., then Part II is added, followed by the remainder of Part III at 70° C. The mixture is cooled slowly with stirring, and a jelly begins to set at about 55° C. The stirring is continued until ambient temperature to ensure good homogeneity. The pH will be between 5.0 and 5.3.

EXAMPLE 31

LOTION FORMULATION

A lotion formulation of 9,11-dichloro-17α-hydroxy-16β-methylpregna-1,4-diene-3,20-dione 17-valerate can be prepared as follows:

| Part I - The following are mixed and melted at 70° C.: | |
|---|---|
| Cetostearyl alcohol ("Lanette O" ®) | 0.65% |
| Ethyleneglycol stearate ("Cutina AGS" ®) | 0.65% |
| Cetostearyl alcohol containing approximately 20 moles ethylene oxide ("Eumulgin B2" ®) | 0.93% |
| Liquid paraffin | 1.95% |
| Part II - Suspend at room temperature: | |
| 9,11-Dichloro-17α-hydroxy-16β-methylpregna-1,4-diene-3,20-dione 17-valerate | the equivalent to 0.1% of the parent steroid |
| Glycerol B.P. | 2.50% |
| Propan-2-ol and ball mill it. | 6.50% |
| Part III - Dissolve at boiling point: | |
| Methyl 4-hydroxybenzoate in | 0.15% |
| Glycerol B.P. | 2.50% |
| Bidistilled water | 84.05% |
| Cool to 70° C. and adjust volume, if necessary. | |

Part III is added to Part I with stirring at 70° C., then Part II is added. The mixture is cooled with efficient stirring to ensure homogeneity.

EXAMPLE 32

OINTMENT FORMULATION

An ointment of dexamethasone 17,21-dipropionate can be prepared as follows:

| | |
|---|---|
| Solid vaseline | 91.8% |
| Liquid paraffin | 8.1% |
| Dexamethasone 17,21-dipropionate | The equivalent to 0.1% of dexamethasone |

The vaseline is melted and maintained at 50° C. with efficient sitrring, whilst a ball-milled suspension of the dexamethasone 17,21-dipropionate in the liquid paraffin is added. The tubes are filled whilst the mixture is still hot and liquid.

EXAMPLE 33

ORAL INHALATION SPRAY FORMULATION

A spray formulation of beclomethasone 17,21-diacetate can be prepared as follows:

| | |
|---|---|
| Beclomethasone 17,21-diacetate (micronised) | 12.06 mg |
| Linoleic acid | 10.00 mg |
| Fluorotrichloromethane | 9990.00 mg |
| Dichlorodifluoromethane | 15000.00 mg |

The linoleic acid is efficiently mixed with cold fluorotrichloromethane, and then the micronised steroid is added. The mixing is continued until a completely uniform mixture is obtained. Any evaporated fluorotrichloromethane must be replaced as necessary. Each inhaler is filled with the required amount, after which the valves are attached and the required dichlorodifluoromethane pumped in.

EXAMPLE 34

INTRAMUSCULAR INJECTION FORMULATION

An intramuscular injection formulation of 21-desoxybetamethasone 17-heptanoate can be prepared as follows:

| | |
|---|---|
| 21-Desoxybetamethasone 17-heptanoate | 1.298 g |
| Sesame oil | 100 ml |

The sterile micronised steroid is efficiently mixed with the sterile sesame oil to ensure a uniform mixture. Each ampoule is filled with 1 ml.

We claim:
1. A process for the preparation of corticosteroid esters of the formula

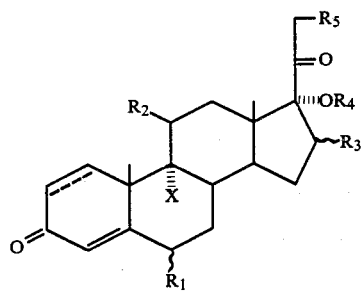

(I)

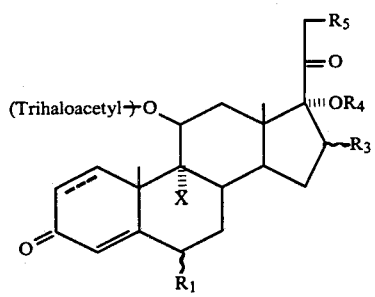

(IV)

in which

- - - - signifies that a double bond can be present;
X is hydrogen, chlorine or fluorine;
$R_1$ is hydrogen, fluorine, chlorine or methyl, which may be either α or β;
$R_2$ is halogen, oxo, or hydroxyl;
$R_3$ is hydrogen, α-methyl or β-methyl; or $R_2$ and X jointly from an epoxide group;
$R_4$ is an acyl group of the formula RCO, in which R is one of the following:
 (i) an alkyl group containing 1 to 16 carbon atoms, whether straight-chained, branched or cyclic;
 (ii) an aralkyl group of 7 to 8 carbon atoms;
 (iii) a phenyl group;
$R_5$ is hydroxyl or $R_6$; where
$R_6$ is hydrogen, one or two halogen atom substituents or $OR_7$, where $R_7$ is an acyl group of the formula R'CO in which R', which can be identical or different to R in the same molecule, is one of the following:
 (i) an alkyl group of 1 to 16 carbon atoms, whether straight-chained, branched or cyclic;
 (ii) an aralkyl group of 7 to 8 carbon atoms; or
 (iii) a phenyl group;
which comprises esterifying a compound of the formula

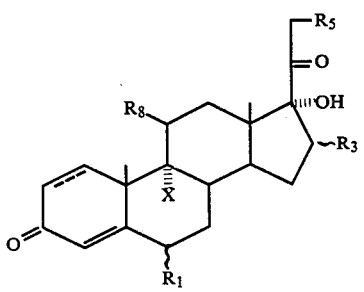

(III)

wherein X, $R_1R_3$ and $R_5$ are as defined above, and
$R_8$ is trihaloacetate, halogen or oxo, or jointly forms an epoxide group with X;
at the 17-position only, or at the 17- and 21-positions when $R_5$ in formula III is hydroxyl, the said esterification being carried out with the anhydride of the acid containing the group desired to enter at the 17-position, or at the 17- and 21-positions, together with a pair of strong acids, and eliminating any 11-trihaloacetate substituent present, to form a compound of formula I.

2. A process according to claim 1, wherein the product of the esterification is a compound of formula IV wherein $R_5$ is $R_6$ and the 11-trihaloacetate group is eliminated by the reaction thereof, in the presence of a lower alcohol, with an organic amine (other than one in which the nitrogen forms a part of an aromatic ring), ammonia gas dissolved in an anhydrous solvent, ammonium hydroxide or hydrazine gas dissolved in an anhydrous solvent, ammonium hydroxide or hydrazine to produce a compound of formula I, wherein $R_2$ is hydroxyl, $R_5$ is $R_6$ and X, $R_1$, $R_3$ and $R_4$ are as defined for formula I.

3. A process according to claim 1, wherein the 11-trihaloacetate group of a compound of formula V

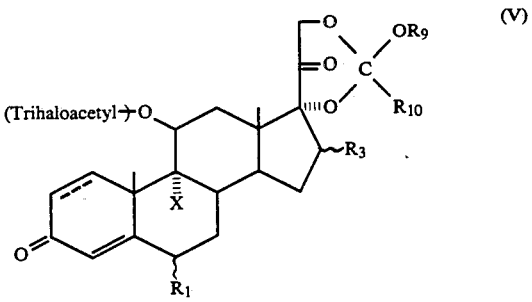

(V)

wherein X, $R_1$ and $R_3$ are as defined for formula I, $R_9$ is an alkyl group of 1 to 3 carbon atoms and $R_{10}$ is an alkyl group of 1 to 16 carbon atoms, whether straight-chained, branched or cyclic, an aralkyl group of 7 to 8 caron atoms, or a phenyl group is eliminated by the reaction thereof, in the presence of a lower alcohol, with an organic amine (other than one in which the nitrogen forms a part of an aromatic ring), ammonia gas dissolved in an anhydrous solvent, ammonium hydroxide or hydrazine to produce a compound of formula I, wherein $R_2$ is hydroxyl, $R_2$ and $R_5$ are hydroxyl, and X, $R_1$, $R_3$ and $R_4$ are as defined for formula I.

4. A process according to claim 1, wherein the compound of the formula III, in which $R_8$ is trihaloacetate, is prepared by the 11-trihaloacetylation of a compound of the formula

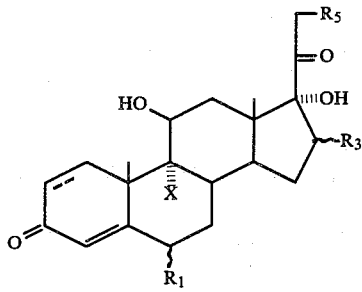

wherein X, $R_1$, $R_3$ and $R_5$ are as defined for formula I.

5. A process according to claims 1 or 4, wherein the trihaloacetate group is trifluoroacetate.

6. A process according to claim 1, wherein at least 1.5 moles of the acid anhydride is used for each mole of the steroid to be esterified.

7. A process according to claim 1, wherein the pair of strong acids is chosen from a trihaloacetic acid plus one of the following: p-toluenesulphonic acid, methanesulphonic acid, benzenesulphonic acid, perchloric acid, and hydrochloric acid.

8. A process according to claim 7, wherein the trihaloacetic acid is trifluoroacetic acid or trichloroacetic acid.

9. A process according to claims 7 or 8, wherein at least 1.5 moles of the trihaloacetic acid is used for each mole of the steroid to be esterified, and the second acid of the pair is present in at least a catalytic quantity.

10. A process according to claim 1, wherein the esterification is effected within the temperature range of 0° C. to 80° C.

11. A process according to claim 10, wherein the esterification is effected within the temperature range of 20° C. to 60° C.

12. A process according to claim 1, wherein the esterification is carried out for 1 to 24 hours, until complete.

13. A process according to claim 1, wherein, after said esterification of a compound of formula III, any 11-trifluoroacetate group is immediately eliminated by one of the following processes:

(a) Treatment with an organic amine, other than an amine in which the nitrogen forms part of an aromatic ring, followed by precipitation in water;
(b) Treatment with a mixture of an organic amine, as defined in (a) above, and of water; or
(c) Treatment with an ammonium hydroxide solution.

14. A process according to claim 1, wherein a primary amine is used to remove the 11-trihaloacetate group.

15. A process according to claim 14, wherein the amine is selected from the group consisting of ethylamine, cyclohexylamine, isopropylamine, n-butylamine, benzylamine and ethanolamine.

16. A process according to claim 1, wherein a secondary amine is used to remove the 11-trihaloacetate group.

17. A process according to claim 16, wherein the amine is selected from the group consisting of diethylamine, diphenylamine, morpholine, piperidine and pyrrolidine.

18. A process according to claim 1, wherein a tertiary amine is used to remove the 11-trihaloacetate group.

19. A process according to claim 18, wherein the amine is selected from the group consisting of triethylamine and triethanolamine.

20. A process according to claim 1, wherein anhydrous ammonia is used to remove the 11-trihaloacetate group and is dissolved in an anhydrous lower alcohol.

21. A process according to claim 20, wherein the lower alcohol is methanol or ethanol.

22. A process according to any one of the claims 13 to 21, wherein the amine, anhydrous ammonia, ammonium hydroxide solution or hydrazine used to remove the 11-trihaloacetate group is present in an amount from catalytic to a slight stoichiometric excess.

23. A process according to claim 1, wherein the removal of the 11-trihaloacetate group is carried out at a temperature from −20° C. to the reflux temperature of the medium.

24. A process according to claim 23, wherein the temperature is from 10° C. to 25° C.

25. 9α-Fluoro-11β,17α,21-trihydroxy-16α-methyl-pregna-1,4-diene-3,20-dione 17-butyrate 21-acetate.

* * * * *